US00PP21516P2

(12) United States Plant Patent
Dekker

(10) Patent No.: US PP21,516 P2
(45) Date of Patent: Nov. 23, 2010

(54) ***CHRYSANTHEMUM* PLANT NAMED 'DEKNYAKA'**

(50) Latin Name: *Chrysanthemum×morifolium*
Varietal Denomination: Deknyaka

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 0 days.

(21) Appl. No.: 12/587,446

(22) Filed: Oct. 7, 2009

(51) Int. Cl.
*A01H 5/00* (2006.01)

(52) U.S. Cl. ..... Plt./294

(58) Field of Classification Search ..... Plt./294
See application file for complete search history.

*Primary Examiner*—Kent L Bell
(74) *Attorney, Agent, or Firm*—C. A. Whealy

(57) ABSTRACT

A new and distinct cultivar of *Chrysanthemum* plant named 'Deknyaka', characterized by its small single-type inflorescences with white-colored ray florets and green-colored disc florets; strong and upright flowering stems; freely branching and flowering habit; early and uniform flowering response; and good postproduction longevity.

2 Drawing Sheets

Botanical designation: *Chrysanthemum×morifolium.*
Cultivar denomination: 'DEKNYAKA'.

BACKGROUND OF THE INVENTION

The present invention relates to a new and distinct cultivar of *Chrysanthemum* plant, botanically known as *Chrysanthemum×morifolium*, commercially grown as a cut flower and hereinafter referred to by the name 'Deknyaka'.

The new *Chrysanthemum* plant is a product of a planned breeding program conducted by the Inventor in Hensbroek, The Netherlands. The objective of the breeding program is to create new freely flowering single-type *Chrysanthemum* plants with unique ray floret coloration and excellent postproduction longevity.

The new *Chrysanthemum* plant originated from a cross-pollination made by the Inventor in Hensbroek, The Netherlands on Sep. 18, 2007 of a proprietary selection of *Chrysanthemum×morifolium* identified as code number 06.51771.02, not patented, as the female, or seed, parent with a proprietary selection of *Chrysanthemum×morifolium* identified as code number 06.48712.01, not patented. The new *Chrysanthemum* plant was discovered and selected by the Inventor as a single flowering plant from within the progeny of the stated cross-pollination in a controlled greenhouse environment in Hensbroek, The Netherlands on Apr. 5, 2008.

Asexual reproduction of the new *Chrysanthemum* plant by terminal cuttings in a controlled greenhouse environment in Hensbroek, The Netherlands since April, 2008, has shown that the unique features of this new *Chrysanthemum* plant are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Deknyaka'. These characteristics in combination distinguish 'Deknyaka' as a new and distinct cultivar of *Chrysanthemum:*

1. Small single-type inflorescences with white-colored ray florets and green-colored disc florets.

2. Strong and upright flowering stems.
3. Freely branching and flowering habit.
4. Early and uniform flowering response; plants flower about 38 to 41 days after the start of photoinductive treatments.
5. Good postproduction longevity; plants maintain good substance for about three weeks in an interior environment.

Plants of the new *Chrysanthemum* differ from plants of the female parent selection in the following characteristics:

1. Plants of the new *Chrysanthemum* have larger inflorescences than plants of the female parent selection.
2. Plants of the new *Chrysanthemum* flower earlier than plants of the female parent selection.

Plants of the new *Chrysanthemum* differ from plants of the male parent selection in the following characteristics:

1. Plants of the new *Chrysanthemum* have smaller leaves than plants of the male parent selection.
2. Plants of the new *Chrysanthemum* have larger inflorescences than plants of the male parent selection.
3. Plants of the new *Chrysanthemum* flower later than plants of the male parent selection.
4. Plants of the new *Chrysanthemum* and the male parent selection differ in ray floret color as plants of the male parent selection have pink-colored ray florets.

Plants of the new *Chrysanthemum* can be compared to plants of *Chrysanthemum×morifolium* 'Deklindi White', disclosed in U.S. Plant Pat. No. 17,815. In side-by-side comparisons conducted in Hensbroek, The Netherlands, plants of the new *Chrysanthemum* differed from plants of 'Deklindi White' in the following characteristics:

1. Plants of the new *Chrysanthemum* were more vigorous than plants of 'Deklindi White'.
2. Plants of the new *Chrysanthemum* were more freely branching than plants of 'Deklindi White'.
3. Plants of the new *Chrysanthemum* flowered about three days later than plants of 'Deklindi White'.

4. Plants of the new *Chrysanthemum* were more freely flowering than plants of 'Deklindi White'.

BRIEF DESCRIPTION OF THE PHOTOGRAPHS

The accompanying colored photographs illustrate the overall appearance of the new *Chrysanthemum* plant. These photographs show the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering stem of 'Deknyaka' grown as a spray type.

The photograph on the second sheet comprises close-up views of the upper (top of photograph) and lower surfaces (bottom of photograph) of typical inflorescences and leaves of 'Deknyaka'.

DETAILED BOTANICAL DESCRIPTION

The aforementioned photographs and following observations and measurements describe plants grown during the summer in Hensbroek, The Netherlands, under commercial practice in a glass-covered greenhouse. Plants were initially given two weeks of long day/short night treatments followed by short day/long night treatments to induce flower initiation and development. During the production of the plants, day temperatures ranged from 18° C. to 25° C., night temperatures ranged from 20° C. to 22° C. and light levels were about 7 kilolux. Plants were pinched one time and were eight weeks from planting when the photographs and the description were taken. In the following description, color references are made to The Royal Horticultural Society Colour Chart, 2001 Edition, except where general terms of ordinary dictionary significance are used.

Botanical classification: *Chrysanthemum×morifolium* 'Deknyaka'.

Parentage:

*Female, or seed, parent.*—Proprietary selection of *Chrysanthemum×morifolium* identified as code number 06.51771.02, not patented.

*Male, or pollen, parent.*—Proprietary selection of *Chrysanthemum×morifolium* identified as code number 06.48712.01, not patented.

Propagation:

*Type.*—Terminal vegetative cuttings.

*Time to initiate roots, summer.*—About four days at 20° C.

*Time to initiate roots, winter.*—About six days at 20° C.

*Time to produce a rooted young plant, summer.*—About 13 days at 20° C.

*Time to produce a rooted young plant, winter.*—About 15 days at 20° C.

*Root description.*—Fine, fibrous; light brown in color.

*Rooting habit.*—Freely branching, moderately dense.

Plant description:

*Appearance/growth habit.*—Herbaceous single-type cut flower that is typically grown as a spray-type; moderately vigorous growth habit.

*Flowering stem description.*—Aspect: Erect. Length: About 60 cm. Spray diameter: About 15 cm to 18 cm. Diameter: About 5 mm to 6 mm. Lateral branch length: About 20 cm to 30 cm. Internode length: About 2 cm. Texture: Finely pubescent; longitudinally ridged. Color: Close to 144A.

*Foliage description.*—Arrangement: Alternate; simple. Length: About 3.5 cm to 7 cm. Width: About 1.5 cm to 3 cm. Apex: Rounded to cuspidate. Base: Attenuate. Margin: Palmately lobed, serrate to crenate; sinuses divergent to parallel. Texture, upper and lower surfaces: Pubescent, slightly rough; veins prominent on lower surface. Venation pattern: Pinnate, reticulate. Color: Developing leaves, upper surface: Close to 137C. Developing leaves, lower surface: Close to 137D. Fully developed leaves, upper surface: Close to N137C; venation, close to 148C. Fully developed leaves, lower surface: Close to 147B; venation, close to 147B to 147C. Petiole: Length: About 5 mm to 15 mm. Diameter: About 1.5 mm to 2.5 mm. Texture, upper and lower surfaces: Slightly rough. Color, upper surface: Close to 146C. Color, lower surface: Close to 146D.

Inflorescence description:

*Appearance.*—Single-type inflorescence form with oblong-shaped ray florets; inflorescences borne on terminals, arising from leaf axils; ray and disc florets develop acropetally on a capitulum.

*Fragrance.*—Slightly fragrant.

*Flowering response.*—Under natural conditions, plant flower in the autumn/winter in the Northern Hemisphere; at other times of the year, inflorescence initiation and development can be induced under short day/long night conditions (at least 13.5 hours of darkness); early and uniform flowering response; plants exposed to eight days of long day/short night conditions after planting followed by photoinductive short day/long night conditions flower about 38 to 41 days later when grown as a spray-type.

*Postproduction longevity.*—In an interior environment, inflorescences and foliage will maintain good color and substance for about three weeks; inflorescences persistent.

*Quantity of inflorescences.*—Freely flowering habit; when grown as a spray type, about 95 inflorescences per flowering stem develop.

*Inflorescence size.*—Diameter: About 2 cm to 2.5 cm. Depth (height): About 1 cm. Disc diameter: About 7 mm to 9 mm. Receptacle height: About 2.5 mm to 3 mm. Receptacle diameter: About 3 mm. Receptacle color: Close to 144B.

*Inflorescence buds.*—Shape: Oblate. Height: About 2 mm. Diameter: About 4 mm. Color: Between 144A and 137C.

*Ray florets.*—Length: About 8 mm to 12 mm. Width: About 4 mm to 6 mm. Shape: Oblong. Apex: Rounded. Base: Attenuate. Margin: Entire. Angle: Initially upright to close to about 30° from vertical. Texture, upper and lower surfaces: Smooth, glabrous; satiny. Number per inflorescence: About 24 arranged in about two whorls. Color: When opening, upper and lower surfaces: Close to NN155D. Fully opened, upper and lower surfaces: Close to NN155D.

*Disc florets.*—Shape: Fused tubular, elongated. Apex: Dentate. Length: About 3 mm. Diameter: About 0.5 mm to 1 mm. Number per inflorescence: About 200, massed at the center. Color: Apex: Close to 144C. Mid-section: Close to 5B. Base: Close to 145D.

*Involucral bracts.*—Length: About 5 mm to 7 mm. Width: About 3 mm to 4 mm. Shape: Ovate. Apex: Rounded. Base: Rounded to truncate. Margin: Entire. Texture, upper and lower surfaces: Smooth, glabrous. Number per inflorescence: About 20 to 25 arranged in about two to three whorls. Color, upper surface: Close to 137A. Color, lower surface: Close to N137B.

*Peduncles.*—Length, terminal peduncle: About 6 cm. Length, fourth peduncle: About 7 cm. Length, seventh peduncle: About 8 cm. Diameter: About 1.5 mm. Angle: Erect to about 30° from vertical. Strength: Moderately strong to strong. Texture: Slightly pubescent; longitudinally ridged. Color: Close to 146B.

*Reproductive organs.*—Androecium: Not observed. Gynoecium: Present on both ray and disc florets. Style length: About 3 mm. Style color: Close to 145D. Stigma color: Close to 154A.

*Seed/fruit.*—Seed and fruit production has not been observed.

Disease/pest resistance: Resistance to pathogens and pests common to *Chrysanthemums* has not been observed on plants grown under commercial conditions.

It is claimed:

1. A new and distinct *Chrysanthemum* plant named 'Deknyaka' as illustrated and described.

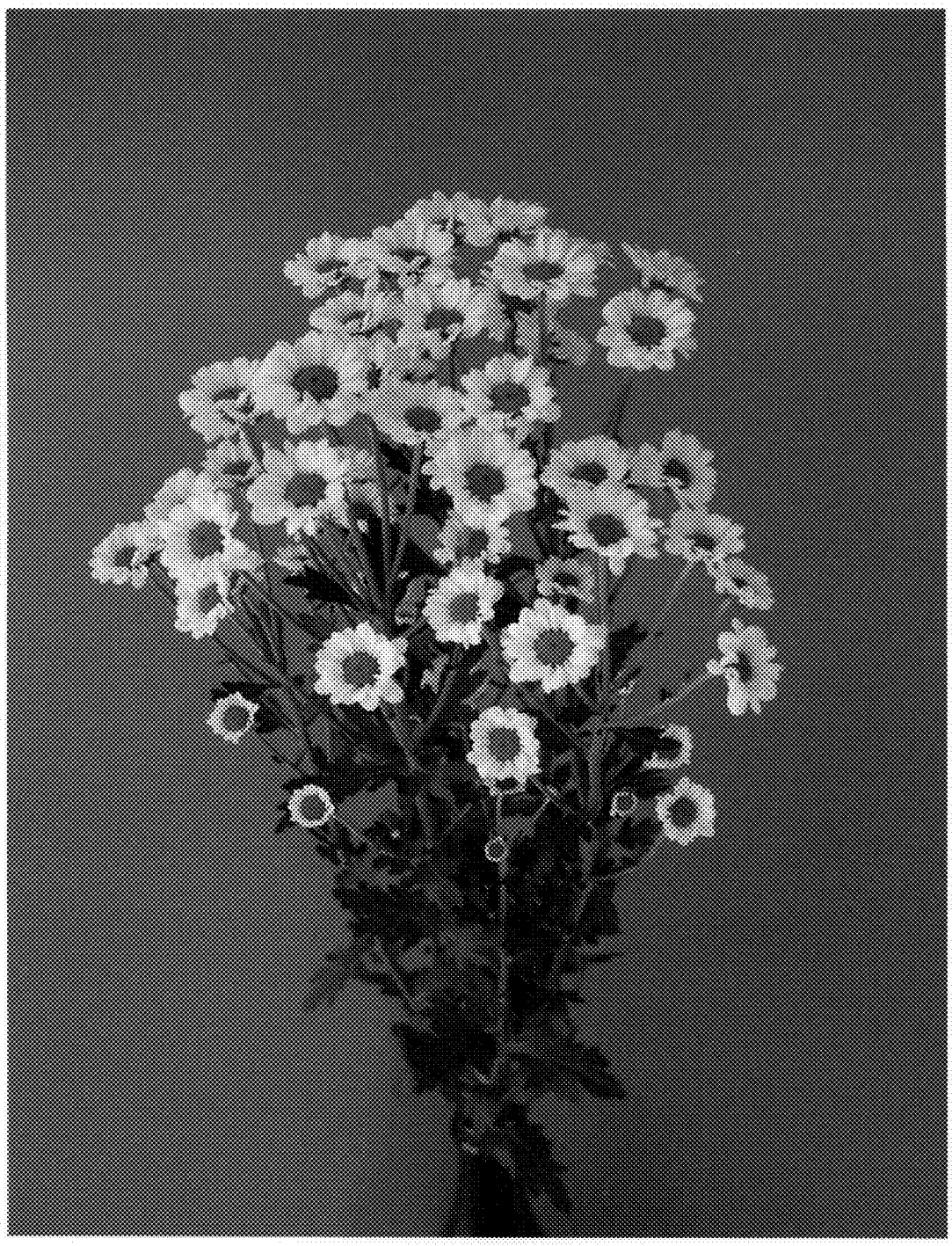

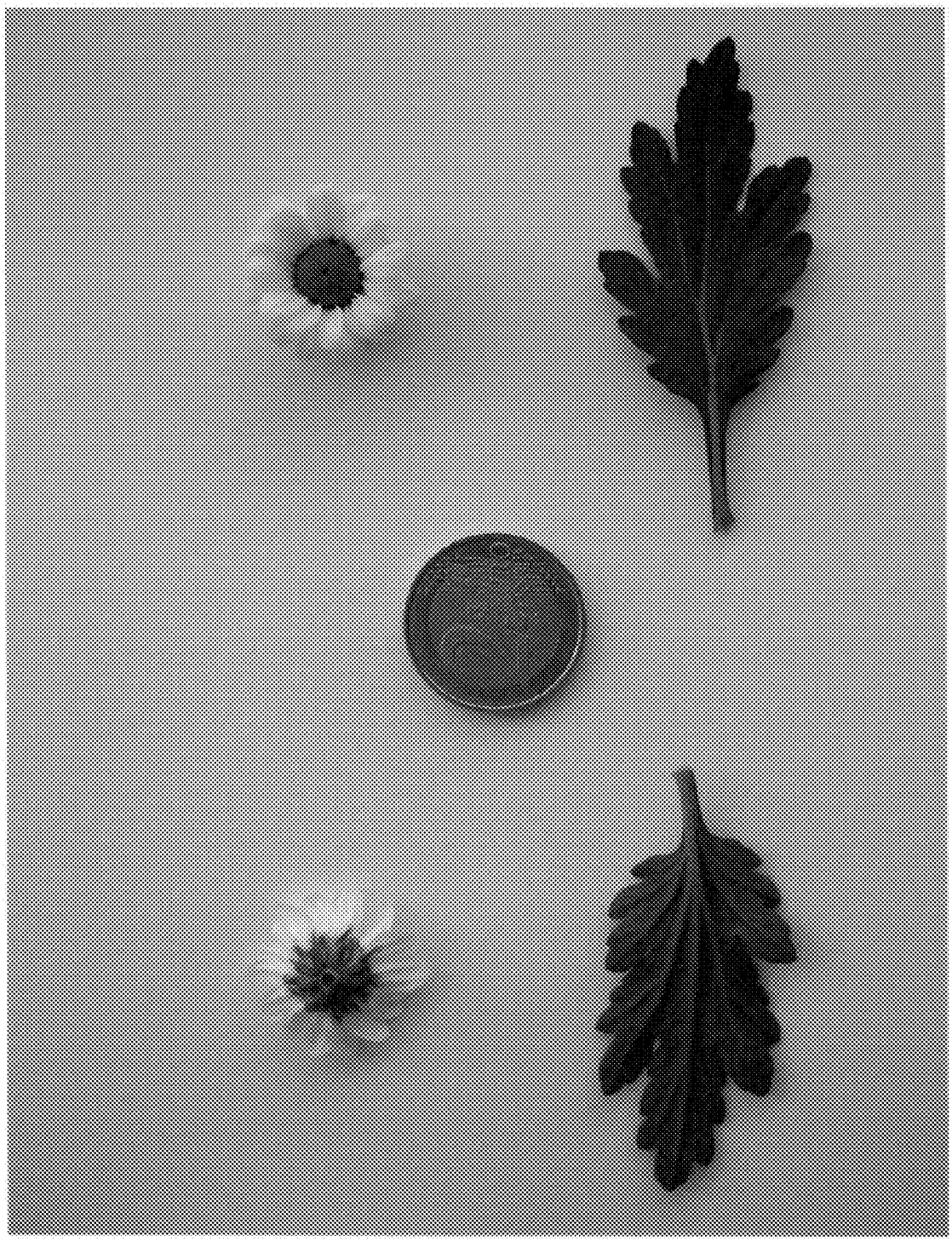

* * * * *